United States Patent [19]

Horan

[11] Patent Number: 5,753,285
[45] Date of Patent: May 19, 1998

[54] METHOD FOR DETERMINING BACTERIA CONTAMINATION IN FOOD PACKAGE

[76] Inventor: Thomas J. Horan, 3111 Rowena Dr., Los Alamitos, Calif. 90720

[21] Appl. No.: 720,217

[22] Filed: Sep. 26, 1996

Related U.S. Application Data

[63] Continuation of Ser. No. 389,296, Feb. 16, 1995, abandoned.

[51] Int. Cl.$^6$ .................................................. A23L 1/00
[52] U.S. Cl. ........................ 426/87; 426/383; 426/415
[58] Field of Search .......................... 426/87, 383, 415

[56] References Cited

U.S. PATENT DOCUMENTS

| | | | |
|---|---|---|---|
| 3,899,295 | 8/1975 | Halpern | 23/253 TP |
| 3,946,611 | 3/1976 | Larsson | 73/356 |
| 4,094,642 | 6/1978 | Sumimoto et al. | 23/254 R |
| 4,205,043 | 5/1980 | Esch et al. | 422/56 |
| 4,222,745 | 9/1980 | Cloyd | 23/230 |
| 4,269,804 | 5/1981 | Kring | 422/86 |
| 4,271,121 | 6/1981 | Diller et al. | 422/56 |
| 4,285,697 | 8/1981 | Neary | 23/230 LC |
| 4,328,181 | 5/1982 | Anders et al. | 422/56 |
| 4,746,616 | 5/1988 | Honigs et al. | 436/20 |
| 4,987,849 | 1/1991 | Sherman | 116/206 |
| 5,053,339 | 10/1991 | Patel | 436/2 |
| 5,096,813 | 3/1992 | Krumhar et al. | 435/28 |
| 5,128,106 | 7/1992 | Buschmann et al. | 422/119 |
| 5,228,573 | 7/1993 | Pavelle et al. | 206/459.1 |
| 5,407,829 | 4/1995 | Wolfbeis et al. | 436/1 |

*Primary Examiner*—Lien Tran
*Attorney, Agent, or Firm*—Henry D. Coleman; R. Neil Sudol

[57] ABSTRACT

A method for determining the presence or absence of contaminating bacteria in a packaged food sample includes storing food in a package having as a lining a polymeric composition, said composition preferably being permeable to at least one gas selected from the group consisting of carbon dioxide and sulfur dioxide and containing an indicator for detecting the presence or abscence of the gas; the indicator being polymerized or dispersed throughout the polymeric composition or coated onto the polymeric composition.

15 Claims, No Drawings

METHOD FOR DETERMINING BACTERIA CONTAMINATION IN FOOD PACKAGE

This application is a continuation of application Ser. No. 08/389,296, filed Feb. 16, 1995, now abandoned.

FIELD OF THE INVENTION

This invention relates to methods for detecting the existence of harmful levels of bacterial growth in packaged foods.

BACKGROUND OF THE INVENTION

The presence of undesirable bacteria, for example, Botulism sp., among others, in food products intended for human consumption has recently caused increased concern among food product manufacturers. This is due to the potential that contaminated food has for serious illness or even death as a consequence of its ingestion by the consumer. While it would be desirable to monitor contamination in every sample of food, in most cases, it is simply not possible to detect the presence of contaminating bacteria by visual or other inspection. Consequently, chemical means must be used to facilitate such detection.

Although food is generally inspected prior to its being canned, it is presently not practical to inspect each can of food for contamination.

OBJECTS OF THE INVENTION

It is an object of the invention to provide a method for detecting the presence of contaminating bacteria in a food sample, especially a food sample which has been stored in cans or other packages.

It is also an object of the present invention to provide new food storage cans which have been adapted to detect the presence of contaminating bacteria in food stored in cans.

It is also an object of the present invention to provide new polymeric compositions which can be incorporated onto the lining of a food can and used to detect contaminating bacteria in canned food.

These and other objects of the present invention may be readily gleaned from the description of the invention which follows.

SUMMARY OF THE INVENTION

The present invention relates to a method for determining the presence or absence of contaminating bacteria in a canned food sample comprising storing food in a can having as a lining a polymeric composition, said composition preferably being permeable to at least one gas selected from the group consisting of carbon dioxide, sulfur dioxide and ammonia gas and containing an indicator for detecting the presence or abscence of said gas; said indicator being polymerized or dispersed throughout said polymeric composition. Alternatively, the indicator may be coated onto the polymeric composition and used directly without further modification or coated in combination with or coated by a permeable polymer which helps the indicator to adhere to the first coating either in combination with the permeable polymer or underneath the permeable polymer.

The present invention also relates to novel food cans which have been lined with polymeric compositions containing an indicator which has been polymerized or dispersed throughout or coated onto the polymeric composition, the food cans being capable of storing food and detecting the presence of gas released by contaminating bacteria present in the food which is stored in the cans.

The present invention is useful for detecting bacterial contamination in food which has been stored after canning or packaging for extended periods of time. Although virtually any microorganism which produces a gas during growth and/or metabolism may be detected by the present invention, particularly important microorganisms which may be detected by the present invention include bacteria such as Salmonella sp., Streptococcus sp., Shigella sp., Botulism sp., *Escherichia coli* and Coliform bacteria. A number of types of *E. coli* may be detected by the instant invention including enterotoxigenic (ETEC), enteroinvasive (EIEC), enterohemorrhagic (EHEC), enteropathogenic (EPEC) and enteradherent (EAEC), among others.

Numerous polymeric compositions for lining the food storage package may be used, with preferred compositions including polymeric compositions which are sufficiently permeable to allow gas produced by contaminating bacteria to diffuse through the composition to a reactive site on an indicator dispersed or polymerized throughout the composition without allowing the food stored within the package to leak or come into contact with a package lining to be avoided, such as the steel lining of a food can.

Indicators include those which are well known in the art. The indicators which find use in the present invention are those which provide a calorimetric reaction upon exposure to the gases produced by contaminating microorganisms. Gases which are produced by contaminating microorganisms include, for example, carbon dioxide, sulfur dioxide and ammonia. Each of these gases in water produces an acid (carbonic, sulfuric) or a base (ammonia) which reacts with the chosen indicator to produce a calorimetric reaction, thus indicating the presence or absence (in the case where no reaction occurs) of contaminating bacteria.

DETAILED DESCRIPTION OF THE INVENTION

The following terms will be used throughout the specification to describe the present invention.

The term "polymeric composition" is used to describe the chemical lining of the food storage containers or plastic wrap according the present invention which contains indicator, whether polymerized or dispersed within the composition or coated onto the composition. Polymeric compositions for use in the present invention include those which are typically used to line cans or make food wrap, for example, polyvinyl acetate, polyvinylchloride copolymers of polyvinylacetate and polyvinylchloride and hydroxyl-modified vinyl chloride/vinyl acetate copolymers (for example, vinyl VAGH and VyHH copolymers available from Union Carbide). Additional, preferred polymers include those which are permeable to one or more of carbon dioxide, sulfur dioxide or ammonia gas produced by the contaminating bacteria. Additional exemplary polymeric compositions for use in the present invention include for example, polyethylene, polystyrene, polytertiarybutylstyrene, cellulose acetate butyrate, polytetrafluoroethylene, polytetrafluoroethylene/hexafluoropropene copolymers (Teflon FEP), butadiene/styrene copolymers, butadiene/methylstyrene copolymers, poly(meth)acrylates, butadiene/acrylonitrile copolymers, ethylene/propylene copolymers, polybutadiene, polyisoprene, polyester resins, poly(imino(1-oxohexamethylene) (Nylon 6), poly(imino(1-oxoundecamethylene) (Nylon 11), poly(oxy2,6-dimethyl-1, 4-phenylene), poly(oxycarbonyloxy-1,4-[1, 4phenyleneisopropylidene-1,4-phenylene) (Lexan), cellulose acetate, ethyl cellulose, polyethylene terephthalate and mixtures, thereof, among others.

The polymeric compositions may be hydrophilic or hydrophobic, but preferably, are hydrophobic in order to minimize the likelihood that the food or water in the food will come into contact with the metal lining of the storage can or the composition will absorb significant quantities of water from the food. In certain cases, for example, when carbon dioxide or sulfur dioxide is to be analyzed, it may be advantageous to have the polymeric composition accommodate or contain small amounts of water, in order to allow the formation of carbonic acid or sulfuric acid, which will be directly detected by the indicators included in the polymeric compositions.

The polymeric composition may line a food package, e.g., a steel can, in a manner to form a "tight coating", i.e., a coating which is designed to preclude any part of the stored food from coming into contact with the underlying can. The polymeric composition may be chosen so as to allow gases to pass through and come into contact with an indicator which has been polymerized or dispersed throughout the polymeric composition. Alternatively, the indicator may be coated onto the polymeric composition and used directly or coated onto the underlying polymeric composition in combination with or underneath a gas permeable polymer which holds the indicator in place for analysis.

One of ordinary skill in the art, simply relying on readily available information regarding the permeability data (for individual gases such as carbon dioxide, sulfur dioxide and ammonia) for the various polymeric compositions and the relative degree of hydrophobicity or hydrophilicity may easily determine the appropriate polymeric composition to use in a particular manner with a particular foodstuff. Thus, one of ordinary skill in the art may choose the appropriate polymeric composition to line the food container, or accommodate an effective amount of indicator based upon the food to be stored as well as a microorganism or bacteria to be detected. For example, in the case of detecting $E.$ $coli$ contamination in cans, one of ordinary skill in the art will recognize that it is appropriate to choose polymers containing an indicator which detects trace quantities of carbon dioxide produced by the bacteria. In the case of other bacteria and foodstuffs, the polymeric composition will be modified to accommodate the appropriate indicator and food.

The term "gas" is used to describe gaseous products of metabolism or growth of contaminating bacteria in food which is stored in the storage cans according to the present invention. Exemplary gases which are detected in the present invention include carbon dioxide, sulfur dioxide and ammonia, among others.

The term "permeable" is used to describe polymeric compositions according to the present invention which allow sufficient quantities of gases to flow through the composition and interact or react with the indicator.

The term "package" is used to describe any container, can, pail, bottle, drum, packing material or wrap in which food may be stored. In the present invention the food package is lined with a polymeric composition which contains or is coated by an indicator. The indicator, where it is coated onto a composition may be further coated with an additional polymeric composition, preferably permeable to the gas or gases to be detected.

The term "contaminating bacteria" is used to describe microorganisms such as bacteria which, if present in food, create a potential health hazard for the consumer. Life-threatening sickness, even death, may result from the consumption of food contaminated with any number of deleterious microorganisms such as bacteria. Although numerous contaminating microoraganisms including bacteria may be detected using the present invention, the most common bacteria which create health problems in food include Salmonella sp., Streptococcus sp., Shigella sp., Botulism sp., $Escherichia$ $coli$ and other Coliform bacteria. In the case of $Escherichia$ $coli$, a number of types may be problematic, but are detected by the present invention including, for example, enterotoxigenic (ETEC), enteroinvasive (EIEC), enterohemorrhagic (EHEC), enteropathogenic (EPEC) and enteradherent (EAEC), among others. Numerous $E.$ $coli$ of O-serogroups may be problematic including for example, (EPEC) 026:K60, 055:K59, 0111:L58, 0127:K63, 086:K61, 0119:K69, 0124:K72, 0125:K70, 0126:K71, 0128:K67, 018:K77, 020:K61, 020:K84, 028:K73, 044:K74, 0112:K66; (ETEC) 06, 08, 011, 078; (EIEC) 028:K73, 0112:K66, 0124:K72, 0143:$K^b$, 0144:$K^c$; and (EHEC) 0157:H7, among others. A particularly onerous serogroup of $E.$ $coli$ is (EHEC) 0157:H7.

The above-referenced bacteria, among others, as a consequence of growth and/or metabolism, produce significant quantities of gas including carbon dioxide, sulfur dioxide or ammonia gas, among others. The gases produced by these deleterious microorganisms may be readily detected using the present invention, thus alerting the consumer to the potential dangers of consuming contaminated food.

The bacteria generally remain dormant as spores in the food product until certain conditions exist. The most prevalent condition is a constant exposure to ambient temperatures of about 45.5° C.+2° C. outside the can, which promotes growth and germination of the bacterial spore. As the bacterial spore grows it releases an effervescent gas, which migrates toward the indicator and produces a chemical reaction.

The term "indicator" is used to describe chemical compounds which may be added to or coated onto polymeric compositions according to the present invention in amounts effective to detect gases which are produced by contaminating bacteria in food. Indicators are chemical compounds which undergo a chemical reaction in the presence of a gas or an acid or base conjugate of a gas and produce a calorimetric species in response to the acid or base produced. The chemical response of the indicator is generally concentration dependent. Indicators for use in the present invention may be solids or liquids. In the present invention, gases which are produced by contaminating bacteria including carbon dioxide, sulfur dioxide and ammonia gas, among others, react with the chosen indicator which has been polymerized or dispersed throughout the polymeric composition. The indicator produces a calorimetric reaction upon exposure to the gas or an acid or base conjugate of the gas, thus evidencing the presence of contaminating bacteria in the analyzed food sample. In certain preferred versions of the present invention, the indicator will produce an irreversible calorimetric reaction upon exposure to the gas produced by the contaminating bacteria, thus minimizing the possibility that leakage of the gas from the food storage container will result in a failure to detect contamination.

Exemplary indicators for the detection of carbon dioxide or sulfur dioxide include, for example, xylenol blue (p-Xylenolsulfonephthalein), bromocresol purple (5',55"-Dibromo-o-cresolsulfonephthalein), bromocresol green (Tetrabromo-m-cresolsulfonephthalein), cresol red (o-Cresolsulfonephthalein), phenolphthalein, bromothymol blue (3',3"-Dibromothymolsulfonephthalein), p-naphtholbenzein (4-[alpha-(4-Hydroxy-1-naphthyl) benzylidene]-1(4H)-naphthalenone) and neutral red (3-Amino-7-dimethylamino-2-methylphenazine Chloride), among others. These indicators all provide calorimetric responses to the addition of quanities of acid, in the form of carbonic acid or sulfuric acid (from $CO_2$ or $H_2SO_4$ production by contaminating bacteria). An exemplary indicator for the detection of ammonia produced by contaminating bacteria comprises a mixture of potassium iodide, mercuric (III) iodide, sodium borate, sodium hydroxide and water (in the ratio of 1.5:2.5:2.5:3.5:90 parts by weight).

Indicators which are advantageouusly employed in the present invention may be dispersed or polymerized throughout the polymeric composition or alternatively, simply coated onto the polymeric composition (lining of the food package). In the case of indicators which are polymerized throughout the polymeric composition, the indicators may be modified and placed in monomeric form in order to participate in the polymerization reaction and become part of a backbone or sidechain of the polymeric composition.

The present invention may be used in standard food cans or alternatively, may be used in other packing materials, such as plastic bags (especially in the case of sea food), saran wrap or cellophane or moisture barrier packing (in the case of storing meats, cheese, poultry, etc.).

In one aspect, the present invention is essentially a warning system for the presence of certain contaminants within containers of processed or non-processed comestibles. A positive analysis will alert a consumer to avoid eating contaminated food.

The uniqueness of this invention is manifest in the following exemplary manner:

1) The capability of ascertaining the presence or absence of contaminants within a container while the contents are in a closed and sealed atmosphere by way of an on-going, and continuous analysis procedure. 2) The container is prepared for the continuing analysis procedure during the manufacturing process where the polymeric composition containing indicator may be applied, directly onto the package or over a standard package (can) coating with a clear USDA or FDA approved indicator solution suspended or dispersed in the polymeric composition and applied by various methods to the package, e.g., sprayed, roller coated, printed, stamped, etc. The polymeric composition containing the indicator will dry, polymerize, convert or cross-link at the specification of the container fill line.

During the container manufacture procedure, the indicator solution, being clear when applied, may be printed or otherwise applied, over standard internal can coatings so as to convey a message to whomever opens the container. Exemplary messages may read:

WARNING! DO NOT EAT THE CONTENTS OF THIS CAN, or

WARNING! BEFORE EATING, THE CONTENTS OF THIS CAN MUST BE HEATED TO 150° F. FOR FIVE MINUTES, or

WARNING! DO NOT EAT, RETURN TO STORE FOR REFUND.

When applied, the indicator is still clear or a particular color which evidences that no reaction or contamination has occurred. When the food package is filled, closed and sealed, the continuing chemical analysis begins. If the food package contains contaminated toxic organic materials, these will begin to grow and multiply within the closed and sealed atmosphere, producing any one or more of carbon dioxide, sulfur dioxide or ammonia, among others during metabolic processes.

The microrganism growth particles may be spores or bacteria which produce gas as they grow and multiply. As the gas accumulates, it migrates in an upward direction to accumulate in a top end area. As the gas contacts the indicator, the indicator ink and gas react, thus causing the indicator to change from a clear or original color to a predetermined color, thus making the warning legible. If no gas is produced, there will be no reaction.

This invention may also be employed in additional applications. Employing the polymeric composition containing an indicator on the inside of a container, i.e., a can, jar lid, bottle cap, 5 gallon pail cover or 55 gallon drum lid, among other packages, the indicator or polymeric composition containing indicator may be deposited on either or both sides of "plastic wrap" sheets or rolls. With both sides of the plastic material printed, when used as a wrapper for table ready comestibles, the user applying the wrap to the food product will not be confused as to which side of the plastic wrap has been printed because the indicator is applied to both sides of the plastic wrap.

As in the instance of comestibles packaged in cans for sale to the general public or for temporary storage in large open containers in processing plants or retail markets, the organisms generate gases as they grow and multiply. The gases will migrate to the indicator and produce a calorimetric reaction, thus, preferably causing a warning to appear.

The following examples are provided to illustrate the present invention and should not be misunderstood to limit the scope of the present invention in any way.

EXAMPLE

The following is a description of the manufacturing process of a standard can that can be used in the packaging of vegetables such as corn, various kinds of beans, fruit, fruit sald, puddings, etc.

The raw material generally is a mild steel in large rolls delivered to the manufacturing site. A large roll is fed into the "slitter." The roll is then "slit" (cut), then rerolled in to various rolls, the width of which is equal to the exact height of the can in its finished state. A roll of the desired width is then painted with a vinyl paint (polyvinyl acetate or polyvinylchloride), the formula of which is compatible with the food product which is to be packaged in the finished can.

The roll is thereafter straightened and cut. The pieces are the exact size of the finsished can body. The pieces are stacked and portions of the stacks are introduced into a feeding device which is a gravity feeder inserting one body piece a time into a machine which forms the flat piece (blank) into a cylinder and passes the now cyclical "body" past an electrical resistance welder, joining the two edges together with an electrical resistance weld. The welded section is then coated with a "side seam enamel" which can tolerate the very high temperature of the welding process.

The welded cyclinder (body) moves along with the conveyer at the speed of of 400–600 can bodies per minute. The conveyor by design changes the direction of the "lie" of the can body. To this point, the can bodies have been in a horizontal position, following each other along the conveyor. They are now turned in a manner to create a side by side relationship, and then fed into a large platen with wide holes. The platen is turning in the same direction as the conveyor. As the platen turns, it takes the cans out of the conveyor line, the inside of the can is sprayed with a vinyl coating, and then the can is returned to the conveyor, the can body now moves along the conveyor a short distance. The solvent formula of the coating is adjusted to the speed of the conveyor and the distance traveled to the oven.

The body is then made. There are generally two and three piece can assemblies. Various formulas are used in the internal finish of the cans. Some have 100% solids and need no "flash off time." Other coatings may employ thermal conversion, chemical reactions or ultra violet light to ensure complete polymerization.

A two piece can involves a body made by deep draw. This method of manufacture would have a single piece deep drawn in the center of the flat stock resulting in a body with the bottom intact in a single impact referred to as a "deep draw." This can be accomplished singularly or by a multiple impact changing tools as the draw is deepened to a desired depth or height of the can. Three piece cans, the most widely-used design, involves a body, a bottom and a top.

The top and bottom of the can are both refrred to as lids, and are made from a single sheet of steel which is die cut to obtain a maximum number of lids per piece of sheet stock. Tops and bottoms are separated from the flash and they are printed with the indicator directly or along with the polymeric composition containing the indicator on the inside portion of the lids. The indicator applied will be specific for the product canned or may be formulated to be sensitive to several contaminating microorganisms.

The indicator used for a particular canning run must be compatible with the internal can coating and maintain acceptable adhesion whether the product is going to be frozen or cooked at a high temperature. Because the food product inside the can comes in contact with the food, the indicator is classified as a food additive and must meet all standards, as set forth by the FDA for food additives.

In the case of a three part can, there is a bottom, a body and a top. The bottom is attached in one of several methods to the body. The cans are filled with food product and the lid is fastened using an approved method. Some cans containing certain food products may be further processed (cooked) at this point. Other cans have fully processed food filled at the start. The filled can is now ready for labeling, packing and shipping.

During storage, if contaminant bacteria are present in the stored food, the gas produced by the bacteria will produce a reaction in the indicator in the lid (top or bottom) of the can. A color reaction will indicate the presence of deleterious quantities of bacteria, no reaction indicates the food product is safe for consumption.

Food Wrap

Generally, two types of vinyl compounds are used in food wrap, e.g., polyvinyl acetate and polyvinyl chloride. The treatment of either of these vinyl solutions is the same. The indicator, dispersed in a compatible carrier, is blended into the vinyl wrap mixture while the ingredients are in a liquid state. Both solutions together will be further processed until the liquid vinyl compound is processed into sheets, then into rolls.

When the wrap is used to cover food products and contaminant bacteria, if present, commence to grow and generate gases. When the gases reach the food wrap and contact the indicator bearing cover, the indicator will react by changing color. The absence of toxin is evidenced by no reaction.

It is to be understood that the embodiments described hereinabove are for the purposes of providing a description of the present invention by way of example and are not to be viewed as limiting the present invention in any way. Various modifications or changes that may be made to that described hereinabove by those of ordinary skill in the art are also contemplated by the present invention and are to be included within the spirit and purview of this application and the following claims.

I claim:

1. A method for detecting the presence or absence of contaminating bacteria in a stored food sample comprising storing food in a package having as a lining a hydrophilic polymeric composition, said composition absorbing water and being permeable to at least one gas released by said bacteria selected from the group consisting of carbon dioxide, and sulfur dioxide to allow the formation of carbonic acid and sulfuric acid from said respective carbon dioxide and sulfur dioxide gas and containing an amount of an indicator effective for visibly detecting the presence or absence of said gas by directly detecting the presence of said carbonic acid or sulfuric acid; said indicator being polymerized or dispersed throughout said polymeric composition.

2. The method according to claim 1 wherein said bacteria is selected from the group consisting of Salmonella sp., Streptococcus sp., Shigella sp., Botulism sp., *Escherichia coli* and Coliform bacteria.

3. The method according to claim 2 wherein said bacteria is *E. coli* serogroup 0157:H7.

4. The method according to claim 1 wherein said indicator is selected from the group consisting of xylenol blue, bromocresol purple, bromocresol green, cresol red, phenolphthalein, bromothymol blue, p-naphtholbenzein and neutral red.

5. The method according to claim 1 wherein said indicator is a mixture of potassium iodide, mercuric (III) iodide, sodium borate, sodium hydroxide and water.

6. The method according to claim 1 wherein said polymeric composition is selected from the group consisting of polyvinyl acetate, copolymers of vinyl acetate and vinylchloride and hydroxylmodified copolymers of vinyl acetate and vinylchloride.

7. A method for detecting the presence or absence of contaminating bacteria in a stored food sample comprising storing food in a package having as a lining a polymeric composition, said composition being coated on a surface nearest said stored food with a hydrophilic polymeric composition containing an amount of an indicator effective for visibly detecting the presence or absence of a gas released by said bacteria, said gas being selected from the group consisting of carbon dioxide and sulfur dioxide, said hydrophilic polymeric composition absorbing water and being permeable to said gas to allow the formation of carbonic acid and sulfuric acid from said respective carbon dioxide and sulfur dioxide gas, said indicator being polymerized or dispersed throughout said hydrophilic polymeric material and said detecting is done by directly detecting the presence of said carbonic acid or sulfuric acid.

8. The method according to claim 7 wherein said polymeric composition is selected from the group consisting of polyvinyl acetate, copolymers of vinyl acetate and vinylchloride and hydroxylmodified copolymers of vinyl acetate and vinylchloride.

9. A food storage package adapted to detect gas released by bacteria which may contaminate food stored in said package, said package being lined with a hydrophilic polymeric composition which absorbs water and is permeable to at least one gas released by said bacteria selected from the group consisting of carbon dioxide and sulfur dioxide to allow the formation of carbonic acid and sulfuric acid from said respective carbon dioxide and sulfur dioxide gas and containing an amount of an indicator effective for visibly detecting the presence or absence of said gas by directly detecting the presence of said carbonic acid or sulfuric acid; said indicator being polymerized or dispersed throughout said polymeric composition.

10. The food storage package according to claim 9 wherein said bacteria is selected from the group consisting of Salmonella sp., Streptococcus sp., Shigella sp., Botulism sp., *Escherichia coli* and Coliform bacteria.

11. The food storage package according to claim 10 wherein said bacteria is *E. coli*.

12. The food storage package according to claim 10 wherein said bacteria is *E. coli* serogroup 0157:H7.

13. The food storage package according to claim 9 wherein said indicator is selected from the group consisting of xylenol blue, bromocresol purple, bromocresol green, cresol red, phenolphthalein, bromothymol blue, p-naphtholbenzein and neutral red.

14. The food storage package according to claim 9 wherein said indicator is a mixture of potassium iodide, mercuric (III) iodide, sodium borate, sodium hydroxide and water.

15. The package according to claim 9 wherein said polmeric composition is selected from the group consisting of polyvinyl acetate, copolymers of vinyl acetate and vinylchloride and hydroxylmodified copolymers of vinyl acetate and vinylchloride.

* * * * *